(12) United States Patent  
Kitamoto et al.

(10) Patent No.: US 10,458,572 B2  
(45) Date of Patent: Oct. 29, 2019

(54) LIQUID HANDLING DEVICE

(71) Applicant: Enplas Corporation, Saitama (JP)

(72) Inventors: Ken Kitamoto, Saitama (JP); Koichi Ono, Saitama (JP)

(73) Assignee: Enplas Corporation, Saitama (JP)

( * ) Notice: Subject to any disclaimer, the term of this patent is extended or adjusted under 35 U.S.C. 154(b) by 237 days.

(21) Appl. No.: 15/526,498

(22) PCT Filed: Oct. 29, 2015

(86) PCT No.: PCT/JP2015/080577  
§ 371 (c)(1),  
(2) Date: May 12, 2017

(87) PCT Pub. No.: WO2016/076133  
PCT Pub. Date: May 19, 2016

(65) Prior Publication Data  
US 2017/0314704 A1    Nov. 2, 2017

(30) Foreign Application Priority Data

Nov. 14, 2014   (JP) .................. 2014-231743

(51) Int. Cl.  
*B01J 3/00*      (2006.01)  
*B01J 19/00*     (2006.01)  
(Continued)

(52) U.S. Cl.  
CPC ....... *F16K 99/0015* (2013.01); *B01J 19/0093* (2013.01); *B01L 3/502723* (2013.01);  
(Continued)

(58) Field of Classification Search  
CPC .......... B01J 19/0093; B01J 2219/00891; B01J 2219/0095; B01L 2200/0621;  
(Continued)

(56) References Cited

U.S. PATENT DOCUMENTS

2008/0190220 A1* 8/2008 Backes ............. B01L 3/502715  
73/864.81  
2014/0166113 A1* 6/2014 Ono .................. B01L 3/502738  
137/1  
(Continued)

FOREIGN PATENT DOCUMENTS

JP     2001-004628 A    1/2001  
JP     2003-47832 A     2/2003  
(Continued)

OTHER PUBLICATIONS

Extended European Search Report for 15858997.8 dated Mar. 8, 2018.  
(Continued)

*Primary Examiner* — Jennifer Wecker  
(74) *Attorney, Agent, or Firm* — Brundidge & Stanger, P.C.

(57) ABSTRACT

A liquid handling device has an accommodation part for accommodating a liquid, two or more flow paths each opening to a lower part of a side wall surface of the accommodation part, and a liquid movement suppression part that is disposed in the lower part of the side wall between the openings of two of the flow paths that are adjacent to each other and slows or stops the movement of the liquid along the corner formed by the lower surface of the accommodation part and the side wall surface.

2 Claims, 7 Drawing Sheets

(51) Int. Cl.
*B81B 1/00* (2006.01)
*G01N 35/08* (2006.01)
*F16K 99/00* (2006.01)
*G01N 37/00* (2006.01)
*B01L 3/00* (2006.01)

(52) U.S. Cl.
CPC .......... *B01L 3/502738* (2013.01); *B81B 1/00* (2013.01); *B81B 1/002* (2013.01); *G01N 35/08* (2013.01); *G01N 37/00* (2013.01); *B01J 2219/0095* (2013.01); *B01J 2219/00891* (2013.01); *B01L 2200/0621* (2013.01); *B01L 2300/0887* (2013.01); *B01L 2400/0688* (2013.01); *B01L 2400/086* (2013.01); *B81B 2201/051* (2013.01); *B81B 2203/0338* (2013.01); *F16K 2099/0084* (2013.01)

(58) Field of Classification Search
CPC ..... B01L 2300/0887; B01L 2400/0688; B01L 2400/086; B01L 3/502723; B01L 3/502738; B81B 1/00; B81B 1/002; B81B 2201/051; B81B 2203/0338; F16K 2099/0084; F16K 99/0015; G01N 35/08; G01N 37/00
See application file for complete search history.

(56) References Cited

U.S. PATENT DOCUMENTS

| | | | |
|---|---|---|---|
| 2014/0174161 A1* | 6/2014 | Ono | B01J 19/00 |
| | | | 73/64.56 |
| 2014/0186214 A1* | 7/2014 | Momose | B01L 3/502753 |
| | | | 422/68.1 |

FOREIGN PATENT DOCUMENTS

| | | |
|---|---|---|
| JP | 2006-234536 A | 9/2006 |
| JP | 2009-233483 A | 10/2009 |
| JP | 2009-236555 A | 10/2009 |

OTHER PUBLICATIONS

International Search Report from International Application No. PCT/JP2015/080577 dated Jan. 12, 2016.

* cited by examiner

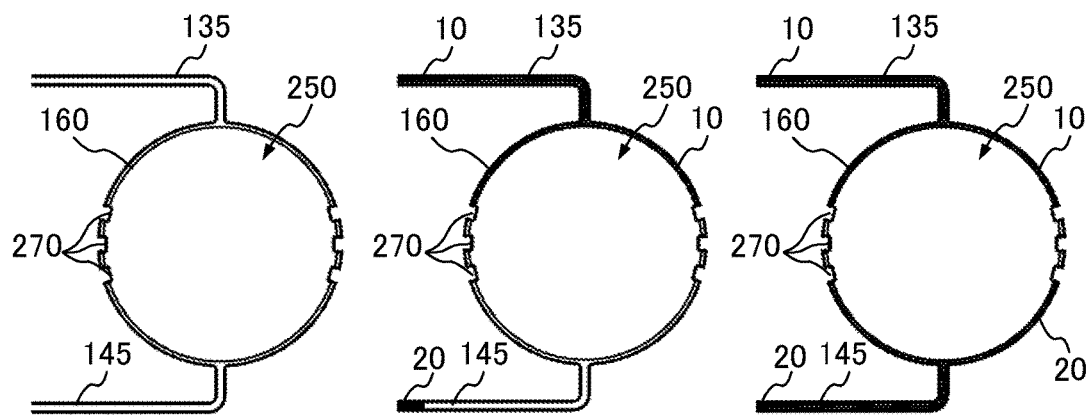

LIQUID HANDLING DEVICE

TECHNICAL FIELD

The present invention relates to a liquid handling device.

BACKGROUND ART

In recent years, microchannel chips have been used to accurately and speedily analyze a trace substance such as protein and nucleic acid. Microchannel chips advantageously allow the amount of reagents or samples required for an analysis to be small, and are expected to be used for various uses such as laboratory tests, food tests, and environment tests. In view of this, microchannel chips of complicated structures and various shapes have been developed (see, for example, PTL 1).

The microchannel chip disclosed in PTL 1 includes four injection hole parts for injecting liquid, four micro channel inflow parts (hereinafter referred to also as "inflow parts"), a micro channel reaction tank part (hereinafter referred to also as "reaction tank part"), a micro channel separation part (hereinafter referred to also as "separation part"), and a waste liquid part. Each of the four injection hole parts, the reaction tank part and the waste liquid part is a bottomed hole formed in a substrate. Solid fine particles are disposed in the reaction tank part for a solid-phase reaction field. The four inflow parts are grooves formed on the substrate. One end of the inflow part is communicated with the reaction tank part, and the other end thereof is communicated with the corresponding one of the four injection hole parts. The separation part is also a groove formed on the substrate. One end of the separation part is communicated with a position facing the inflow part with the reaction tank part therebetween in the reaction tank part, and the other end thereof is communicated with the waste liquid part. Further, the cross-sectional area of the separation part channel is smaller than the diameter of the solid fine particle. With such a configuration, reaction materials introduced from the inflow parts to the reaction tank part are adsorbed on the solid fine particles, and the solid fine particles are blocked without flowing into the separation part. On the other hand, only unreacted materials introduced from the inflow parts to the reaction tank part are allowed to flow into the separation part, and are separated from the reaction tank part to the waste liquid part. In the microchannel chip, reaction materials of three types are introduced from the three inflow parts to the reaction tank part, and reaction is caused in the reaction tank part. After the reaction, the unreacted materials are separated from the separation part, and analysis is performed. It is to be noted that the remaining one inflow part can be used for introducing washing solution. As described above, in the microchannel chip disclosed in PTL 1, reaction materials of two or more types are introduced from two or more inflow parts to the reaction tank part to cause reaction and thus analysis can be performed as desired.

It is to be noted that, in the microchannel chip disclosed in PTL 1, a protection plate may be disposed on the surface of the substrate. The protection plate is provided with openings at positions corresponding to the four injection hole parts, the reaction tank part, and the waste liquid part, and thus the injection hole part, the reaction tank part and the waste liquid part are communicated with the outside. However, the openings of the inflow parts and the separation part which function as the channel are closed with the protection plate.

CITATION LIST

Patent Literature

PTL 1
Japanese Patent Application Laid-Open No. 2001-004628

SUMMARY OF INVENTION

Technical Problem

In the liquid handling device (microchannel chip) disclosed in PTL 1, liquid is introduced from two or more channels (inflow parts) to the housing part (reaction tank part). Normally, the liquid is introduced with a time difference, not simultaneously. Even if it is desired to simultaneously introduce the liquid to the housing part, it is difficult to exactly simultaneously introduce the liquid. For this reason, in some situation, liquid firstly introduced from a certain channel to the housing part can move along the side wall surface of the housing part and close the opening of another channel to the housing part. In this case, the air in the other channel cannot escape to the housing part, and the movement of the liquid in the other channel is stopped, and consequently, analysis cannot be appropriately performed.

An object of the present invention is to provide a liquid handling device which includes two or more channels, and can suppress a situation where liquid introduced from a certain channel to a housing part closes an opening of another channel

Solution to Problem

A liquid handling device of an embodiment of the present invention includes: a housing part for housing liquid; two or more channels opening at a bottom portion of a side wall surface of the housing part; and a liquid movement suppressing part disposed between openings of two of the channels adjacent to each other at the bottom portion of the side wall surface, the liquid movement suppressing part being configured to delay or stop movement of liquid along a corner formed by a bottom surface and the side wall surface of the housing part.

Advantageous Effects of Invention

According to the present invention, it is possible to appropriately introduce liquid from one housing part to two or more channels, and appropriately perform reaction, analysis and the like.

BRIEF DESCRIPTION OF DRAWINGS

FIG. 7A to FIG. 7C are schematic views illustrating a process of introducing liquid to the housing part of the microchannel chip according to Embodiment 2.

DESCRIPTION OF EMBODIMENTS

Embodiments of the present invention are described below in detail with reference to the accompanying drawings. In the following description, a microchannel chip is described as a typical example of a fluid handling device according to embodiments of the present invention.

[Embodiment 1]

In Embodiment 1, a microchannel chip in which a plurality of recesses are formed on a side wall surface of a housing part as a liquid movement suppressing part is described.

(Configuration of Microchannel Chip)

Figure 1A:
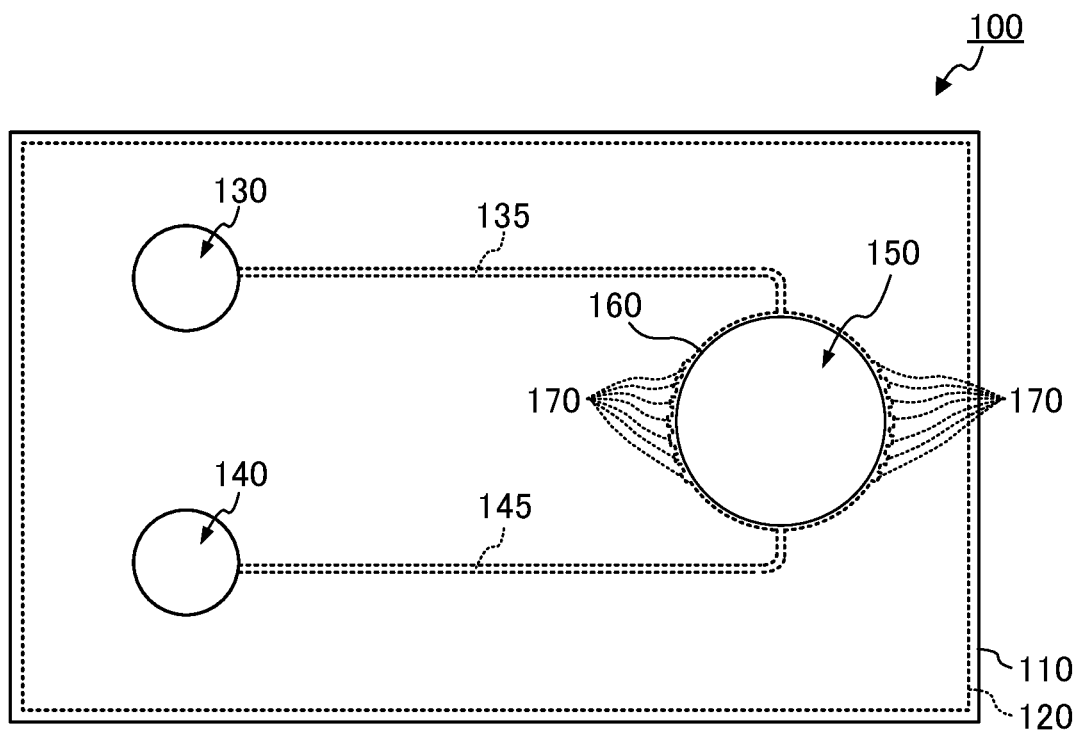
FIG. 1A is a plan view of a microchannel chip according to Embodiment 1.
Figure 1B:
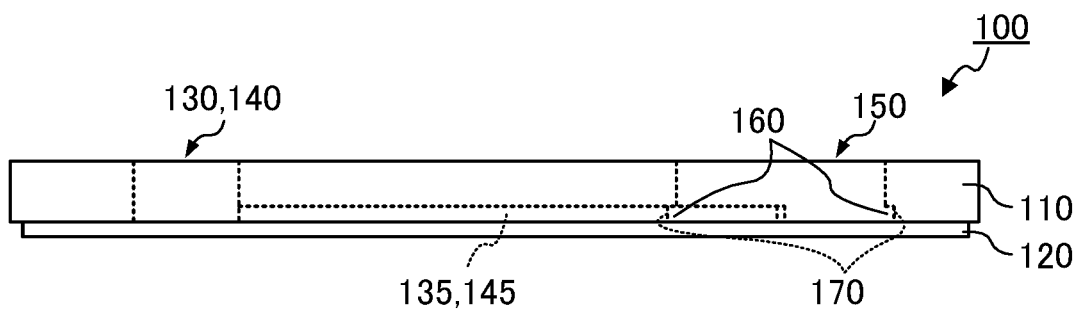
FIG. 1B is a side view of the microchannel chip according to Embodiment 1.
Figure 2:
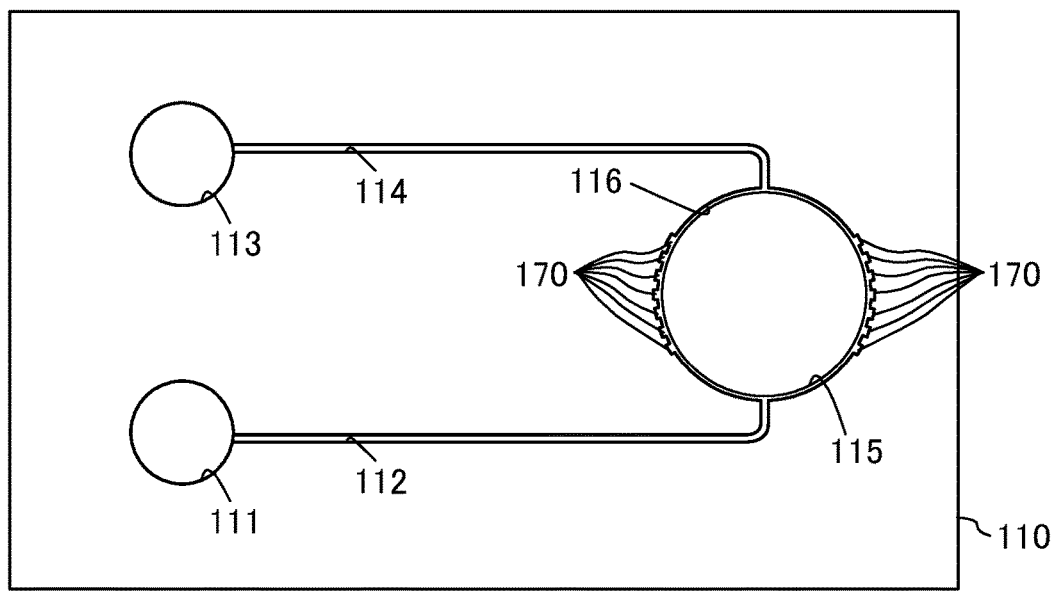
FIG. 2 is a bottom view of a substrate of the microchannel chip according to Embodiment 1.

FIG. 1A and FIG. 1B illustrate a configuration of microchannel chip 100 according to Embodiment 1. FIG. 1A is a plan view of microchannel chip 100, and FIG. 1B is a side view of microchannel chip 100. FIG. 2 is a bottom view illustrating a configuration of substrate 110 of microchannel chip 100 according to Embodiment 1.

As illustrated in FIG. 1A and FIG. 1B, microchannel chip 100 according to the present embodiment is composed of substrate 110 and film 120. In addition, microchannel chip 100 includes first liquid introduction part 130, first channel 135, second liquid introduction part 140, second channel 145 and housing part 150. In housing part 150, circumferential groove 160 and 14 liquid movement suppressing parts 170 are formed.

Substrate 110 is a substantially rectangular transparent plate made of a resin material. As illustrated in FIG. 2, in substrate 110, first through hole 111, first groove 112, second through hole 113, second groove 114, third through hole 115 and third groove 116 are formed. First groove 112, second groove 114 and third groove 116 are formed on one surface (bottom surface) of substrate 110. The both end portions of first groove 112 are communicated with first through hole 111 and third through hole 115 (third groove 116), respectively. In addition, the both end portions of second groove 114 are communicated with second through hole 113 and third through hole 115 (third groove 116), respectively. Third groove 116 is formed at the opening edge of third through hole 115.

The thickness of substrate 110 is not limited. For example, substrate 110 has a thickness of 1 to 10 mm. In addition, the kind of the resin of substrate 110 is not limited, and may be appropriately selected from publicly known resins. Examples of the resin of substrate 110 include polyethylene terephthalate, polycarbonate, polymethylmethacrylate, polyvinyl chloride, polypropylene, polyether, polyethylene, polystyrene, silicone resin, and elastomer. The method of producing substrate 110 is not limited. For example, substrate 110 is produced by injection molding and the like.

Film 120 is a substantially rectangular transparent film made of a resin material. Film 120 is disposed on one surface (bottom surface) of substrate 110. The type of the resin of film 120 is not limited as long as sufficient adhesion to substrate 110 and properties required during analysis such as a heat resisting property and a reagent resisting property can be ensured. Examples of the resin of film 120 include polyethylene terephthalate, polycarbonate, polymethylmethacrylate, polyvinyl chloride, polypropylene, polyether, polyethylene, polystyrene, silicone resin and the like. The thickness of film 120 is not limited as long as the above-mentioned function can be ensured, and can be appropriately set in accordance with the type (rigidity) of the resin. In the present embodiment, film 120 has a thickness of about 20 µm.

Film 120 is joined to the surface (bottom surface) of substrate 110 on which first groove 112, second groove 114 and third groove 116 are formed. When the openings of first groove 112, second groove 114 and third groove 116 are closed with film 120, first groove 112, second groove 114 and third groove 116 serve as first channel 135, second channel 145 and circumferential groove 160, respectively. In addition, when the openings of first through hole 111 and second through hole 113 are closed with film 120, first through hole 111 and second through hole 113 serve as first liquid introduction part 130 and second liquid introduction part 140, respectively. Further, when the opening of third through hole 115 is closed with film 120, third through hole 115 serves as housing part 150 which can house liquid. The method of joining film 120 to substrate 110 is not limited. For example, film 120 can be joined to substrate 110 by thermal welding, laser welding, adhesive agent or the like.

First liquid introduction part 130 and first channel 135 are an inlet and an introduction channel for introducing liquid to housing part 150. The upstream end of first channel 135 is communicated with first liquid introduction part 130, and the downstream end of first channel 135 is communicated with housing part 150. In particular, the downstream end of first channel 135 opens at the bottom portion (lower portion) of the side wall surface of housing part 150.

First liquid introduction part 130 is a recess for housing liquid to be introduced to first channel 135. The shape and the size of first liquid introduction part 130 is not limited as long as liquid can be introduced to first liquid introduction part 130 from the outside. Examples of the shape of first liquid introduction part 130 include a columnar shape, and a truncated cone shape. In the present embodiment, first liquid introduction part 130 has a columnar shape.

First channel 135 moves liquid introduced at first liquid introduction part 130 to housing part 150. First channel 135 moves liquid by capillarity. The cross-sectional area and the cross-sectional shape of first channel 135 are not limited as long as liquid can be moved from first liquid introduction part 130 to housing part 150. For example, the cross-sectional area and the cross-sectional shape of first channel 135 are a nearly rectangular shape whose length (width and depth) of one side is about several micrometers to several millimeters. It is to be noted that the "cross-section of the channel" herein means the cross-section of the channel orthogonal to the flowing direction of the liquid.

Second liquid introduction part 140 and second channel 145 are an inlet and an introduction channel for introducing liquid to housing part 150. The upstream end of second channel 145 is communicated with second liquid introduction part 140, and the downstream end of second channel 145 is communicated with housing part 150. In particular, the downstream end of second channel 145 opens at the bottom portion (lower portion) of the side wall surface of housing part 150.

Second liquid introduction part 140 is a recess for housing liquid to be introduced to second channel 145. The shape and the size of second liquid introduction part 140 are not limited as long as liquid can be introduced to second liquid introduction part 140 from the outside. The shape and the size of second liquid introduction part 140 are similar to those of first liquid introduction part 130. In addition, the shape and the size of second liquid introduction part 140 may be identical to or different from those of first liquid introduction part 130. In the present embodiment, the shape and the size of second liquid introduction part 140 are identical to those of first liquid introduction part 130.

Second channel 145 moves liquid introduced at second liquid introduction part 140 to housing part 150. Second channel 145 moves liquid by capillarity. The cross-sectional area and the cross-sectional shape of second channel 145 are not limited as long as liquid can be moved from second liquid introduction part 140 to housing part 150. The cross-sectional area and the cross-sectional shape of second channel 145 are similar to those of first channel 135. The cross-sectional area and the cross-sectional shape of second channel 145 may be identical to or different from those of first channel 135. In the present embodiment, the cross-sectional area and the cross-sectional shape of second channel 145 are identical to those of first channel 135.

Housing part 150 houses liquid flowing from first channel 135 and second channel 145. The shape, the volume and the like of housing part 150 are not limited, and are appropriately set in accordance with the use. For example, housing part 150 is utilized as a reaction site, a waste liquid part of sample after reaction and the like. In the present embodiment, housing part 150 has a columnar shape. As described above, at the bottom portion of the side wall surface of housing part 150, circumferential groove 160 and 14 liquid movement suppressing parts 170 are disposed. At the bottom portion of the side wall surface of housing part 150 (in the present embodiment, the side wall of circumferential groove 160), the openings of first channel 135 and second channel 145 face each other. Seven liquid movement suppressing parts 170 are disposed in one region at the bottom portion of the side wall surface of housing part 150 (in the present embodiment, the side wall of circumferential groove 160) between the openings of first channel 135 and second channel 145. The remaining seven liquid movement suppressing parts 170 are disposed in the other region at the bottom portion of the side wall surface of housing part 150 between the openings of first channel 135 and second channel 145.

Circumferential groove 160 is disposed such that only the lower end (the outer peripheral edge of the bottom surface of housing part 150) of the side wall surface of housing part 150 is recessed with respect to the entirety of the side wall surface. First channel 135 and second channel 145 open to circumferential groove 160. By capillarity, circumferential groove 160 moves liquid flowing into housing part 150 from first channel 135 or second channel 145.

Figure 3:
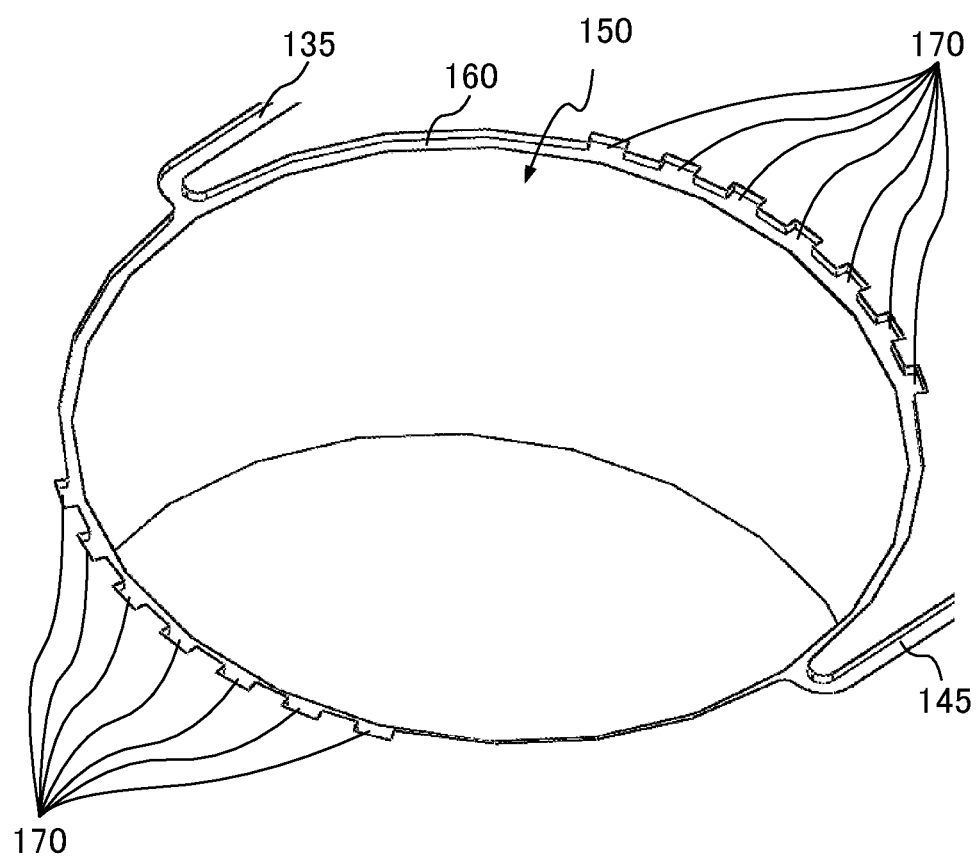
FIG. 3 is a partially enlarged perspective view of a region around a housing part (third through hole) of the substrate of the microchannel chip according to Embodiment 1 as viewed from the bottom surface side.

Liquid movement suppressing parts 170 are protrusions or recesses provided for delaying or stopping movement of liquid along the corner formed by the bottom surface and the side wall surface of housing part 150 (in the present embodiment, circumferential groove 160). In the present embodiment, liquid movement suppressing parts 170 are recesses. FIG. 3 is a partially enlarged perspective view of a region around third through hole 115 (housing part 150) of substrate 110 as viewed from the bottom surface side. The position of liquid movement suppressing parts 170 is not limited as long as the above-mentioned function can be ensured. In the present embodiment, liquid movement suppressing parts 170 are disposed between downstream ends (openings) of first channel 135 and second channel 145 at the bottom portion of the side wall surface of housing part 150 (the opening edge of third through hole 115). In addition, the number and the size of liquid movement of each suppressing part 170 are also not limited as long as the above-mentioned function can be ensured. In the present embodiment, liquid movement suppressing parts 170 are 14 recesses in total. As described above, liquid movement suppressing parts 170 are disposed such that seven movement suppressing parts on both sides face each other at the bottom portion of the side wall surface of housing part 150. The size of each liquid movement suppressing part 170 is appropriately set in accordance with the volume, the viscosity and the like of the liquid which flows thereto. With this configuration, it is possible to adjust the time until liquid, which is introduced from an opening of a channel, reaches an opening of another channel by flowing along the corner formed by the bottom surface and the side wall surface of housing part 150 (in the present embodiment, through circumferential groove 160). In addition, the sizes of liquid movement suppressing parts 170 may be identical to each other or different from each other. In the present embodiment, the sizes of liquid movement suppressing parts 170 are identical to each other. In addition, in the present embodiment, the size of each liquid movement suppressing part 170 is 0.2 mm×0.05 mm×0.04 mm.

(Operation of Microchannel Chip)

Figure 4A:
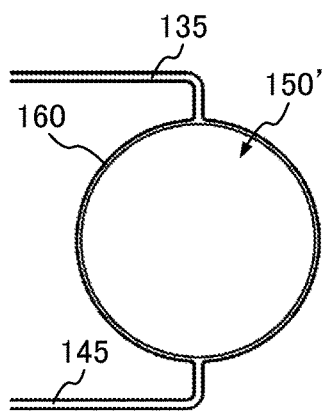
FIG. 4A to FIG. 4C are schematic views illustrating a process of introducing liquid to a housing part of a microchannel chip according to a comparative example.
Figure 4B:
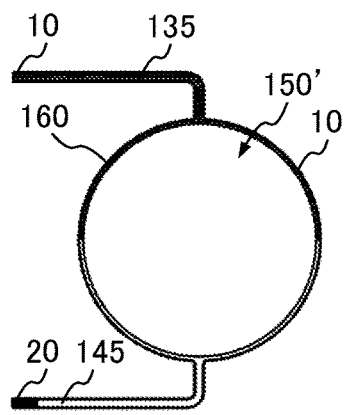
Figure 4C:
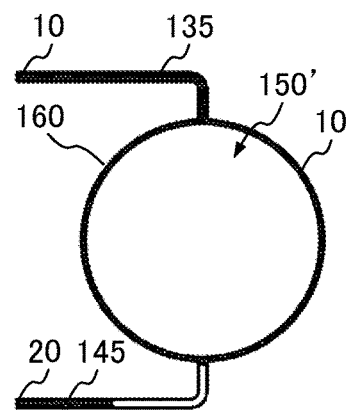
Figure 4D:
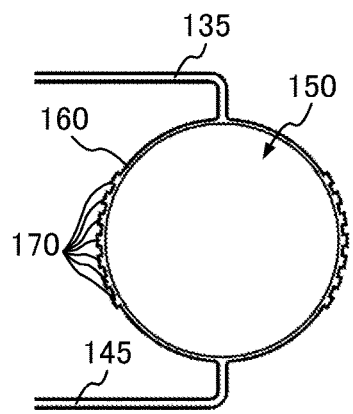
FIG. 4D to FIG. 4F are schematic views illustrating a process of introducing liquid to the housing part of the microchannel chip according to Embodiment 1.
Figure 4E:
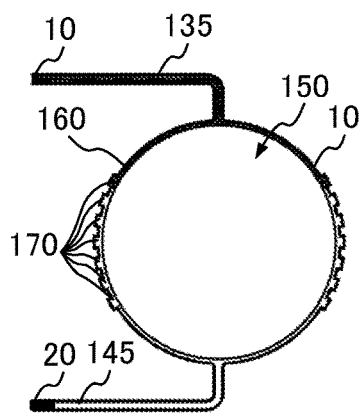
Figure 4F:
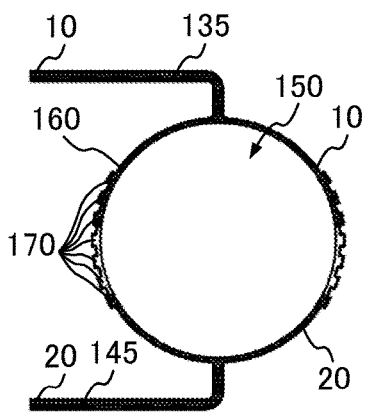

Next, a function of liquid movement suppressing parts 170 when microchannel chip 100 according to the present embodiment is used is described. In addition, for the purpose of describing an effect of liquid movement suppressing parts 170, a microchannel chip according to a comparative example in which liquid movement suppressing parts 170 are not formed at the bottom portion of the side wall surface of housing part 150' is described. FIG. 4A to FIG. 4C are schematic views illustrating a process of introducing liquid to housing part 150' of the microchannel chip according to the comparative example, and FIG. 4D to FIG. 4F are schematic views illustrating a process of introducing liquid to housing part 150 of microchannel chip 100 according to Embodiment 1. It is to be noted that, FIG. 4A to FIG. 4F illustrate only a region around housing parts 150' and 150 of the microchannel chip in an enlarged manner. In addition, here, the liquid flowing through first channel 135 arrives at housing parts 150' and 150 before the liquid flowing through second channel 145 arrives at housing parts 150' and 150.

It is to be noted that the type of liquid to be introduced to first channel 135 (first liquid introduction part 130) and second channel 145 (second liquid introduction part 140) is not limited. Examples of the type of the liquid include a reagent, a liquid sample and the like. In addition, the viscosity of the liquid is not limited as long as the liquid can move in first channel 135 and second channel 145 by capillarity. The type of the liquid to be introduced to first channel 135 (first liquid introduction part 130) may be identical to or different from that of second channel 145 (second liquid introduction part 140). In the following descriptions of the operation of microchannel chip 100, the types of the liquid to be introduced to first channel 135 and second channel 145 are different from each other. Liquid 10 is introduced to first channel 135, and liquid 20 is introduced to second channel 145.

First, with reference to FIG. 4A to FIG. 4C, the microchannel chip according to the comparative example is described. Liquid 10 is introduced to first liquid introduction part 130 not illustrated in the drawing. Almost simultaneously, liquid 20 is introduced to second liquid introduction part 140 not illustrated in the drawing (see FIG. 4A). Next, first channel 135 is filled with liquid 10 by capillarity, and liquid 10 moves toward the downstream end of first channel 135. Simultaneously, second channel 145 is filled with liquid 20 by capillarity, and liquid 20 moves toward the downstream end of second channel 145. Liquid 10 firstly reaching the downstream end of first channel 135 flows into housing part 150'. Liquid 10 flowing into housing part 150' from the downstream end of first channel 135 moves along circumferential groove 160 (see FIG. 4B). Liquid 10 moves along circumferential groove 160, and reaches the downstream end of second channel 145. The opening at the downstream end of second channel 145 is closed with liquid 10 which has moved along circumferential groove 160. As a result, the air in second channel 145 cannot escape to housing part 150', and liquid 20 in second channel 145 cannot move (see FIG. 4C).

Next, with reference to FIG. 4D to FIG. 4F, microchannel chip 100 according to Embodiment 1 is described. Liquid 10 is introduced to first liquid introduction part 130 not illustrated in the drawing. Almost simultaneously, liquid 20 is introduced to second liquid introduction part 140 not illustrated in the drawing (see FIG. 4D). Next, first channel 135 is filled with liquid 10 by capillarity, and liquid 10 moves toward the downstream end of first channel 135. Simultaneously, second channel 145 is filled with liquid 20 by capillarity, and liquid 20 moves toward the downstream end of second channel 145. Liquid 10 firstly reaching the downstream end of first channel 135 flows into housing part 150. Liquid 10 flowing into housing part 150 from the downstream end of first channel 135 moves along circumferential groove 160 (see FIG. 4E). When liquid 10 reaches liquid movement suppressing part 170, a recess serving as liquid movement suppressing part 170 is filled with liquid 10 and liquid 10 moves along circumferential groove 160. Consequently, the movement speed of liquid 10 is reduced. Meanwhile, liquid 20 which has moved in second channel 145 flows into housing part 150 (see FIG. 4F). It is to be noted that in the case where no circumferential groove 160 is formed on the side wall surface of housing part 150, that is, in the case where no recess is formed in the region from the opening edge to the bottom portion at the side wall surface of housing part 150 except for the region where liquid movement suppressing parts 170 are formed, liquid 10 flowing into housing part 150 moves along the corner formed by the side wall surface of housing part 150 and the bottom surface of housing part 150.

As described above, in microchannel chip 100 according to the present embodiment, liquid movement suppressing parts 170 reduce the speed of liquid 10 which moves along the corner formed by the side wall surface of housing part 150 and the bottom surface of housing part 150 (in the present embodiment, liquid 10 which moves in circumferential groove 160 in housing part 150) in comparison with the microchannel chip according to the comparative example provided with no liquid movement suppressing part 170, and it is thus possible to appropriately introduce liquid 10 and liquid 20 from first channel 135 and second channel 145 to housing part 150.

(Effect)

As described above, in microchannel chip (liquid handling device) 100 according to the present embodiment, liquid can be appropriately introduced from two or more channels to one housing part. That is, even in the case where liquid of two or more types (for example, a sample, a reagent and the like) are used, reaction, analysis and the like can be appropriately performed.

[Embodiment 2]

In Embodiment 2, a microchannel chip in which a plurality of protrusions are formed on the side wall surface of a housing part as a liquid movement suppressing part is described.

(Configuration of Microchannel Chip)

Microchannel chip 200 according to the present embodiment differs from microchannel chip 100 according to Embodiment 1 in number and shape of liquid movement suppressing parts 270 in housing part 250. In view of this, the same components as those of microchannel chip 100 according to Embodiment 1 are denoted by the same reference numerals, and the descriptions thereof are omitted.

Figure 5A:
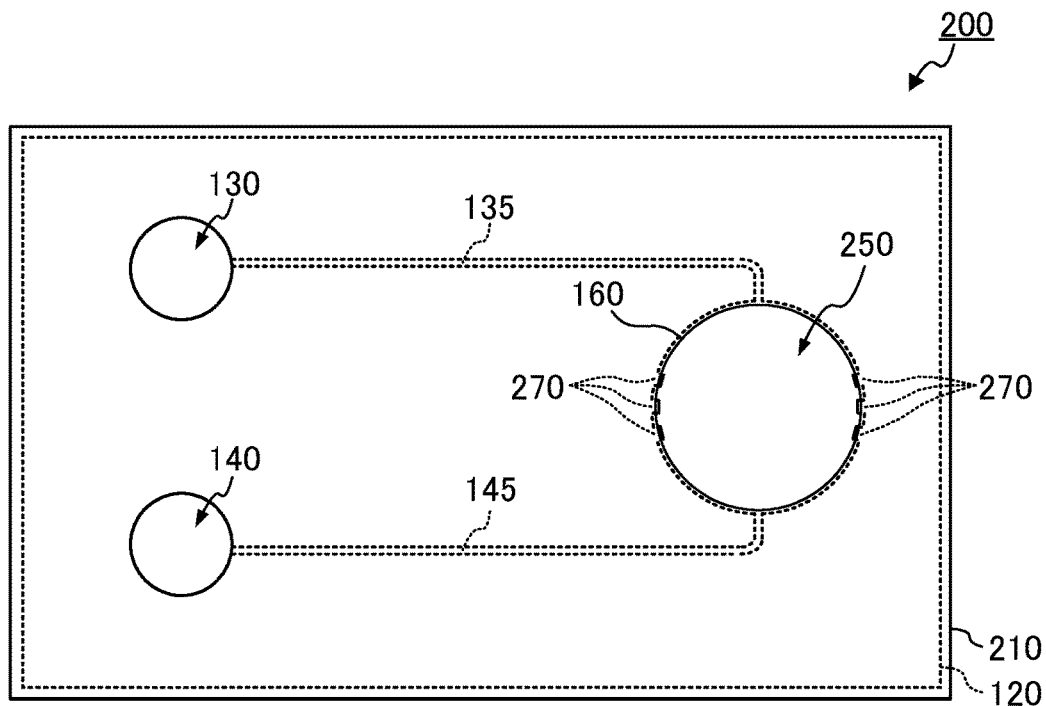
FIG. 5A is a plan view of a microchannel chip according to Embodiment 2.
Figure 5B:
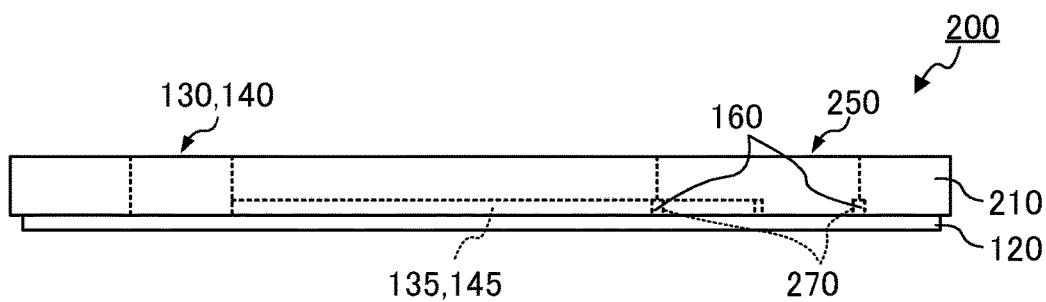
FIG. 5B is a side view of the microchannel chip according to Embodiment 2.

FIG. 5A and FIG. 5B illustrate a configuration of microchannel chip 200 according to Embodiment 2. FIG. 5A is a plan view of microchannel chip 200, and FIG. 5B is a side view of microchannel chip 200.

As illustrated in FIG. 5A and FIG. 5B, microchannel chip 200 according to the present embodiment is composed of substrate 210 and film 120. In addition, microchannel chip 200 includes first liquid introduction part 130, first channel 135, second liquid introduction part 140, second channel 145 and housing part 250. In housing part 250, circumferential groove 160 and six liquid movement suppressing parts 270 are formed.

Housing part 250 is formed when the opening of third through hole 115 formed in substrate 210 is closed with film 120. Housing part 250 houses liquid flowing from first channel 135 and second channel 145. At the bottom portion of the side wall surface of housing part 250, circumferential groove 160 and six liquid movement suppressing parts 270 are disposed. At the bottom portion (lower portion) of the side wall surface of housing part 250, the openings of first channel 135 and second channel 145 face each other. Three liquid movement suppressing parts 270 are disposed in one region at the bottom portion of the side wall surface of housing part 250 between the openings of first channel 135 and second channel 145. The remaining three liquid movement suppressing parts 270 are disposed in the other region at the bottom portion of the side wall surface of housing part 250 between the openings of first channel 135 and second channel 145.

Figure 6:
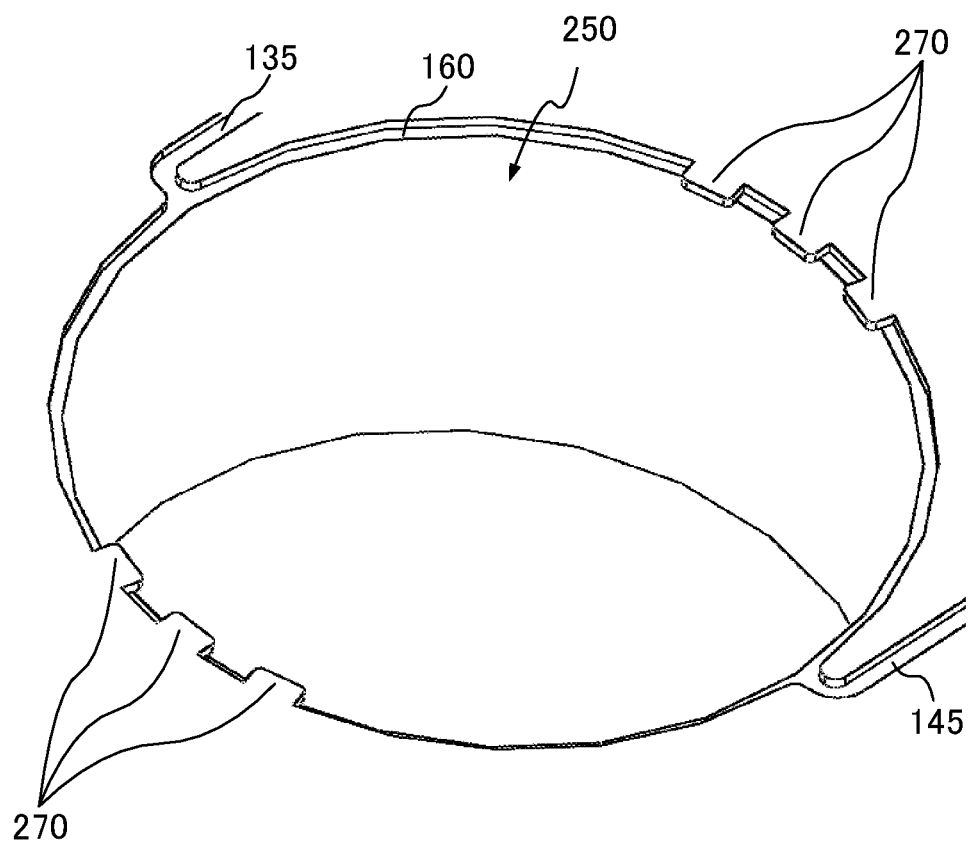
FIG. 6 is a partially enlarged perspective view of a region around a housing part (third through hole) of a substrate of the microchannel chip according to Embodiment 2 as viewed from the bottom surface side.

Liquid movement suppressing parts 270 are protrusions or recesses provided for delaying or stopping the movement of liquid along the corner (circumferential groove 160) formed by the bottom surface and the side wall surface of housing part 250. In the present embodiment, liquid movement suppressing parts 270 are protrusions. FIG. 6 is a partially enlarged perspective view of a region around third through hole 115 (housing part 250) of substrate 110 as viewed from the bottom surface side. The positions of liquid movement suppressing parts are not limited as long as the above-mentioned function can be ensured. In the present embodiment, liquid movement suppressing parts 270 are disposed between the downstream ends (openings) of first channel 135 and second channel 145 at the bottom portion of the side wall surface of housing part 250 (the opening edge of third through hole 115). In addition, the number and the size of liquid movement suppressing parts 270 are not limited as long as the above-mentioned function can be ensured. In the present embodiment, liquid movement suppressing parts 270 are six protrusions in total. As described above, liquid movement suppressing parts 270 are disposed such that three movement suppressing parts on both sides face each other at the bottom portion of the side wall surface of housing part 250. The size of each liquid movement suppressing part 270 is appropriately set in accordance with the volume, the viscosity and the like of the liquid which flows thereto. With this configuration, it is possible to adjust the time until liquid, which is introduced from an opening of a channel, reaches an opening of another channel by flowing along the corner formed by the bottom surface and the side wall surface of housing part 150 (in the present embodiment, through circumferential groove 160). In addition, the sizes of liquid movement suppressing parts 270 may be identical to each other or different from each other. In the present embodiment, the sizes of liquid movement suppressing parts 270 are identical to each other. In addition, in the present embodiment, the size of each liquid movement suppressing part 270 is 0.2 mm×0.1 mm×0.04 mm.

(Operation of Microchannel Chip)

Next, a function of liquid movement suppressing parts 270 when microchannel chip 200 according to the present embodiment is used is described. FIG. 7A to FIG. 7C are schematic views illustrating a process of introducing liquid to housing part 250 of microchannel chip 200 according to Embodiment 2. It is to be noted that FIG. 7A to FIG. 7C illustrate only a region around housing part 250 in a microchannel chip in an enlarged manner. In addition, here, liquid 10 flowing through first channel 135 arrives at housing part 250 before liquid flowing through second channel 145 arrives at housing parts 250.

Liquid 10 is introduced to first liquid introduction part 130 not illustrated in the drawing. Almost simultaneously, liquid 20 is introduced to second liquid introduction part 140 not illustrated in the drawing (see FIG. 7A). Next, first channel 135 is filled with liquid 10 by capillarity, and liquid 10 moves toward the downstream end of first channel 135. Simultaneously, second channel 145 is filled with liquid 20 by capillarity, and liquid 20 moves toward the downstream end of second channel 145. Liquid 10 firstly reaching the downstream end of first channel 135 flows into housing part 250. Liquid 10 flowing into housing part 250 from the downstream end of first channel 135 moves along circumferential groove 160 (see FIG. 7B). However, liquid 10 cannot go over the protrusion serving as liquid movement suppressing part 270, and therefore cannot move in circumferential groove 160 thereafter. Meanwhile, liquid 20 which has moved in second channel 145 can flow into housing part 250 (see FIG. 7C).

As described above, in microchannel chip 200 according to the present embodiment, liquid movement suppressing parts 270 can stop the movement of liquid 10 in circumferential groove 160 in housing part 250, and thus liquid 10 and liquid 20 can be appropriately introduced from first channel 135 and second channel 145 to housing part 250.

(Effect)

As described above, microchannel chip (liquid handling device) 200 according to the present embodiment can appropriately introduce liquid from two or more channels to one housing part. That is, even in the case where liquid of two or more types (for example, a sample, a reagent and the like) are used, reaction, analysis and the like can be appropriately performed.

In the embodiments, two or more liquid movement suppressing parts 170 and 270 are disposed to face each other at the bottom portion of the side wall surface of housing parts 150 and 250 in microchannel chips 100 and 200. Alternatively, the microchannel chip according to the embodiments of the present invention may be provided with only one liquid movement suppressing part. In this case, the openings of the first channel opening and the second channel do not face each other at the side wall surface of the housing part. The one liquid movement suppressing part is installed in a shorter circumferential groove of two circumferential grooves located between the opening of the first channel and the opening of the second channel While microchannel chips 100 and 200 include two channels in the embodiments, the number of channels of the liquid handling device according to the embodiments the present invention is not limited as long as two or more channels are provided. In this case, the liquid movement suppressing part is disposed between the openings of two channels adjacent to each other.

While circumferential groove 160 is formed in microchannel chips 100 and 200 in the embodiments, circumferential groove 160 may not be formed in the microchannel chip according to the embodiments of the present invention. In this case, liquid moves along the corner formed by the bottom surface and the side wall surface of the housing part.

While liquid movement suppressing parts 170 and 270 are a recess or a protrusion formed on the side wall surface of housing parts 150 and 250 in microchannel chips 100 and 200 in the embodiments, the liquid movement suppressing part may be a recess formed on the outer periphery part of the bottom surface of the housing part in the liquid handling device according to the embodiments of the present invention. In this case, a recess which serves as the liquid movement suppressing part is formed on the film. This recess delays or stops the movement of liquid along the corner formed by the bottom surface and the side wall surface of the housing part.

This application is entitled to and claims the benefit of Japanese Patent Application No. 2014-231743 filed on Nov. 14, 2014, the disclosure each of which including the specification, drawings and abstract is incorporated herein by reference in its entirety.

INDUSTRIAL APPLICABILITY

The liquid handling device of the present invention is useful as a microchannel chip used in the scientific fields, the medical fields and the like, for example.

REFERENCE SIGNS LIST 10, 20 Liquid
100, 200 Microchannel chip
110, 210 Substrate
111 First through hole
112 First groove
113 Second through hole
114 Second groove
115 Third through hole
116 Third groove
120 Film
130 First liquid introduction part
135 First channel
140 Second liquid introduction part
145 Second channel
150, 150', 250 Housing part
160 Circumferential groove
170, 270 Liquid movement suppressing part

The invention claimed is:
1. A liquid handling device comprising:
a housing part for housing liquid;
two or more channels opening at an edge of a side wall surface of the housing part; and a circumferential groove disposed between openings of two of the two or more channels adjacent to each other and disposed along the edge of the side wall surface of the housing part; and a liquid movement suppressing part including:
at least one recess recessed radially outward from an outer circumference, of the circumferential groove, or
at least one protrusion protruding toward the housing part from the outer circumference of the circumferential groove, wherein the liquid movement suppressing part being configured to delay or stop movement of liquid along the circumferential groove.

2. The liquid handling device according to claim 1 further comprising:

a substrate including a through hole and two or more grooves whose end portion is connected with an edge of one opening of the through hole; and a film disposed on one surface of the substrate such that the film closes the one opening of the through hole and openings of the two or more grooves, wherein:

the housing part is formed when the one opening of the through hole is closed with the film, the channel is formed when the openings of the grooves are closed with the film, the circumferential groove is formed at the edge of the opening of the through hole, and the liquid movement suppressing part is a recess or a protrusion formed at the circumferential groove.

* * * * *